(12) United States Patent
Berezhnyy et al.

(10) Patent No.: US 9,572,715 B2
(45) Date of Patent: Feb. 21, 2017

(54) SYSTEMS, DEVICES, AND METHODS FOR CALIBRATION OF BEAM PROFILERS

(71) Applicant: AMO Manufacturing USA, LLC, Santa Ana, CA (US)

(72) Inventors: Ihor Berezhnyy, Los Gatos, CA (US); Anthony Tang, San Jose, CA (US); Henry Price, San Jose, CA (US)

(73) Assignee: AMO Manufacturing USA, LLC, Santa Ana, CA (US)

( * ) Notice: Subject to any disclaimer, the term of this patent is extended or adjusted under 35 U.S.C. 154(b) by 3 days.

(21) Appl. No.: 14/808,869

(22) Filed: Jul. 24, 2015

(65) Prior Publication Data

US 2016/0025555 A1    Jan. 28, 2016

Related U.S. Application Data

(60) Provisional application No. 62/029,164, filed on Jul. 25, 2014.

(51) Int. Cl.
| | |
|---|---|
| *G01J 1/00* | (2006.01) |
| *A61F 9/008* | (2006.01) |
| *G01J 1/42* | (2006.01) |
| *G01M 11/06* | (2006.01) |
| *G01J 1/58* | (2006.01) |

(52) U.S. Cl.
CPC .............. *A61F 9/008* (2013.01); *G01J 1/4257* (2013.01); *G01J 1/58* (2013.01); *G01M 11/061* (2013.01); *A61F 2009/00855* (2013.01)

(58) Field of Classification Search
CPC  G01N 21/274; G01N 21/6452; G01N 35/028; G01N 21/6486; G01N 2035/0405; G01N 2035/0425; G01N 2021/6439; G01N 2035/00366; G01N 35/1074; G01N 2035/00287; G01N 2035/1039; G01N 21/276; G01N 21/27
See application file for complete search history.

(56) References Cited

U.S. PATENT DOCUMENTS

| | | | |
|---|---|---|---|
| 6,377,298 B1 | 4/2002 | Scheele et al. | |
| 7,990,460 B2 | 8/2011 | Wenstrand et al. | |
| 2016/0022492 A1* | 1/2016 | Berezhnyy | A61F 9/00802 606/5 |

* cited by examiner

*Primary Examiner* — Michael P Stafira
(74) *Attorney, Agent, or Firm* — Abbott Medical Optics Inc.

(57) ABSTRACT

Embodiments generally describe systems, devices, and methods for focusing and calibrating beam profilers. A test object is provided that may include an internal housing rotatable within an external housing. The internal housing may house a light source, a collimator, a filter, and/or a diffuser. A plate may be mounted to the internal housing and may include a plurality of markings. In some embodiments, to focus a beam profiler, the test object may be positioned adjacent the converter plate of a beam profiler. Marker images may be captured and a focus quality may be assessed therefrom. A position of the converter, objective, and/or camera of the beam profiler may be adjusted based on the focus quality. To calibrate, images of the markings in several rotational positions may be captured and used for calibration. The markings may be rotated to several positions by rotating the internal housing relative to the external housing.

17 Claims, 10 Drawing Sheets

Figure 17

SYSTEMS, DEVICES, AND METHODS FOR CALIBRATION OF BEAM PROFILERS

CROSS REFERENCE TO RELATED APPLICATIONS

The present application claims the benefit of U.S. Provisional Patent Application No. 62/029,164 filed Jul. 25, 2014, the disclosure of which is incorporated herein by reference in its entirety.

BACKGROUND OF THE INVENTION

The present invention generally relates to beam profiler systems and more particularly to systems and methods for focusing and geometrically calibrating a beam profiler.

A UV light beam profiler is a metrological imaging tool for determination of geometrical parameters of a beam profile, such as, size, position, uniformity, shape, and others. It may be used in military, medical, and commercial applications where precise control of UV light beam parameters is desired. Like other metrological devices, the beam profiler should be calibrated every time after assembly, repair (e.g., component replacement or the like), alignment, realignment, and for verification sake. This calibration requirement may be costly, time intensive, or not readily possible if the beam profiler cannot be easily removed from the field or an integrated system. Additionally, for some beam profilers to work properly, the beam profiler should be focused properly.

BRIEF SUMMARY OF THE INVENTION

The terms "invention," "the invention," "this invention" and "the present invention" used in this patent are intended to refer broadly to all of the subject matter of this patent and the patent claims below. Statements containing these terms should be understood not to limit the subject matter described herein or to limit the meaning or scope of the patent claims below. Embodiments of the invention covered by this patent are defined by the claims below, not this summary. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings and each claim.

There is a need for a tool that can be used for beam profiler focusing and focus verification. Additionally, it may be advantageous if the tool can perform geometrical calibration of a beam profiler in the field without having to remove the beam profiler from the host system. Such a tool may avoid the need for beam profiler removal from a host system and beam profiler shipping to a manufacturer for calibration. In some embodiments, it may be advantageous if the tool is compact and inexpensive and can be used anywhere the beam profiler is installed.

Accordingly, in some embodiments of the present invention, a focusing and/or calibration tool is provided. The focusing or geometric calibration test object may be used with a beam profiler, for example. In some embodiments, the object may include an external housing and an internal housing rotatably mounted within the external housing and rotatable relative to the external housing about an internal housing axis. The test object may further include a light source housed within the internal housing and a plate coupled with the internal housing and transverse to the internal housing axis. The plate may include a plurality of markings on the plate.

In some embodiments, the test object may further include a light diffuser housed in the internal housing and positioned between the light source and the plate. The diffuser may be configured to disperse light from the light source across the markings on the plate.

Optionally, the light source may be configured to output light in a broad spectral range and the test object may also include a bandpass filter housed in the internal housing and positioned between the light source and the plate. The bandpass filter may be configured to selectively transmit light from the light source in a particular range of wavelengths.

In some embodiments, a collimating lens may be positioned between the light source and the plate. The collimating lens may be configured to collimate the light emitted by the light source.

Optionally, the light source may be configured to output light in a narrow bandwidth. In such an embodiment, the test object may not include a bandpass filter.

In some embodiments, the plate may be positioned at a first end of the internal housing. An outer face of the plate may be even with a first end of the external housing.

A second end of the internal housing opposite the first end of the internal housing may include one or more indicia. A second end of the external housing opposite the first end of the external housing may also have one or more indicia. The indicia on the second end of the internal housing and the indicia on the second end of the external housing may cooperate to provide rotation information (e.g., a degree of rotation) between the internal housing and the external housing.

In some embodiments, the plurality of markings may be separated by a known distance. The plurality of markings may be a repeated bar pattern. The repeated bar pattern may include major bars and minor bars indicating different units of length.

Optionally, the plurality of markings on the plate may be a resolution test chart.

In some embodiments, the external housing and the internal housing comprise cylindrical housings.

In further embodiments, a beam profiler system may be provided that includes a UV-to-visible converter plate. The UV-to-visible converter plate may be configured to emit fluorescing light when excited by UV radiation. The profiler may further include an image sensor and a lens for imaging a profile of the fluorescing light from the UV-to-visible converter onto the image sensor. The UV-to-visible converter plate and the lens may be moveable relative to the image sensor.

The beam profiler system may further include a focusing and geometric calibration test object for use with the beam profiler. The test object may include an external housing and an internal housing rotatably mounted within the external housing. The internal housing may be rotatable relative to the external housing about an internal housing axis. A light source may be provided and housed within the internal housing. A plate may be coupled with the internal housing and transverse to the internal housing axis and a plurality of markings may be on the plate.

The beam profiler may further include a filter positioned between the UV-to-visible converter plate and the image sensor. The filter may be configured to selectively transmit light to the image sensor.

Optionally the test object may include a light diffuser, and a collimating lens housed in the internal housing and positioned between the light source and the plate. The diffuser may be configured to disperse light from the light source across the markings on the plate, and the collimating lens may be configured to collimate the light emitted by the light source.

The light source may be configured to output light in a broad spectral range. The test object may include a bandpass filter configured to selectively transmit light from the light source in a particular range of wavelengths.

Optionally the diffuser may be positioned between the plate and the bandpass filter. The bandpass filter may be positioned between the diffuser and the collimator. The collimator may be positioned between the light source and the bandpass filter.

In some embodiments, the light source may be configured to output light in a narrow bandwidth and the test object may not include a bandpass filter.

The lens and the image sensor of the beam profiler may be along a single axis with the converter plate of the beam profiler. The lens and the image sensor of the beam profiler may measure light fluoresced from a surface of the converter plate.

The lens and the converter plate may be fixed together to form a lens-converter plate assembly and the lens-converter plate assembly may move relative to the image sensor of the beam profiler for focusing the beam profiler.

In further aspects, a method of focusing and/or calibrating a beam profiler using a test object is provided. The test object may include an external housing, an internal housing rotatably mounted within the external housing and rotatable relative to the external housing about an internal housing axis, a light source housed within the internal housing, an plate coupled with the internal housing and transverse to the internal housing axis, and a plurality of markings on the plate. The method may include (a) positioning the plate of the test object adjacent to a UV-to-visible converter plate of the beam profiler; (b) imaging the plurality of markings on the plate of the test object with the beam profiler; (c) determining a focus quality of the image of the plurality of markings; and (d) adjusting a distance between the UV-to-visible converter plate of the beam profiler and an objective lens of the beam profiler.

The method may include repeating steps (b)-(d) until a desired focus of the beam profiler is obtained.

Optionally, the method may include energizing the light source of the test object prior to imaging the plurality of markings on the plate of the test object.

The method may further include: (e) imaging the plurality of markings on the plate of the test object with the beam profiler with the plurality of markings at a first position; (f) rotating the internal housing relative to the external housing by a rotational amount to rotate the plurality of markings on the plate to a rotated position; (g) imaging the plurality of markings on the plate at the rotated position with the beam profiler; and (h) geometrically calibrating the beam profiler based on the image of the test object at the first position, the image of the test object at the rotated position, and the rotational amount.

Optionally, the method may include repeating steps (f)-(g) so as to provide a plurality of images of the test object at various rotated positions. A calibration of the beam profiler may be based on the image of the test object at the first position, the plurality of images of the test object at various rotated positions, and the rotational amounts.

In further aspects of the invention, a method of focusing and/or calibrating a beam profiler using a test object is provided. The method may include positioning the plate of the test object adjacent to a UV-to-visible converter plate of the beam profiler and imaging the plurality of markings on the plate of the test object at a first orientation with the beam profiler. The method may further include rotating the internal housing relative to the external housing by a rotational amount to rotate the plurality of markings on the plate to a rotated position and imaging the plurality of markings on the plate of the test object at the rotated position with the beam profiler. The beam profiler may be geometrically calibrated based on the image of the plurality of markings at the first orientation, the image of the plurality of markings at the rotated position, and the rotational amount. In some embodiments, the method may further include energizing the light source of the test object prior to imaging the plurality of markings on the plate of the test object.

In further aspects of the invention, a calibration and/or focusing tool for use with a laser eye surgery system is provided. The laser eye surgery system may have a UV laser, a beam splitter, and a beam fluence profiler having a camera and a fluorescent plate. The tool may include a housing mountable to the laser surgery system and a plate having reference markings for identification of locations across two dimensions. The plate may be supported by the housing so as to be adjacent the fluorescent plate of the beam fluence profiler when the housing is mounted to the system such that the markings are imaged by the camera.

In further aspects, a system for focusing a beam profiler using a test object is provided. The system may include a processing device and a non-transitory computer-readable medium accessible by the processing device. The processing device may be configured to execute logic embodied in the non-transitory computer-readable medium and thereby perform operations including (a) imaging the plurality of markings on the plate of the test object with the beam profiler at a first position when the plate of the test object is adjacent to a UV-to-visible converter plate of the beam profiler; (b) determining a focus quality of the image of the plurality of markings; (c) outputting a signal corresponding the determined focus quality of the image of the plurality of markings to an operator, the signal being indicative of a need to adjust a distance between the UV-to-visible converter plate of the beam profiler and an objective lens of the beam profiler; (d) receiving input related to a rotational amount in which the internal housing is rotated relative to the external housing to rotate the plurality of markings on the plate to a rotated position; (e) imaging the plurality of markings on the plate at the rotated position with the beam profiler; and (f) geometrically calibrating the beam profiler based on the image of the test object at the first position, the image of the test object at the rotated position, and the input related to the rotational amount.

The invention will be better understood upon reading the following description and examining the figures which accompany it. These figures are provided by way of illustration only and are in no way limiting on the invention.

DETAILED DESCRIPTION OF THE INVENTION

The subject matter of embodiments of the present invention is described here with specificity, but this description is not necessarily intended to limit the scope of the claims. The claimed subject matter may be embodied in other ways, may include different elements or steps, and may be used in conjunction with other existing or future technologies. This description should not be interpreted as implying any particular order or arrangement among or between various steps or elements except when the order of individual steps or arrangement of elements is explicitly described.

Figure 1:
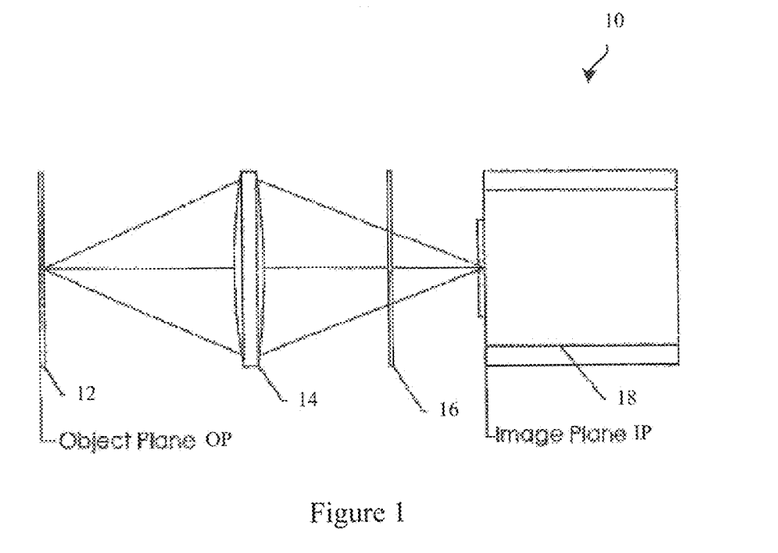
FIG. 1 illustrates a side view of an exemplary UV light beam profiler.
Figure 2:
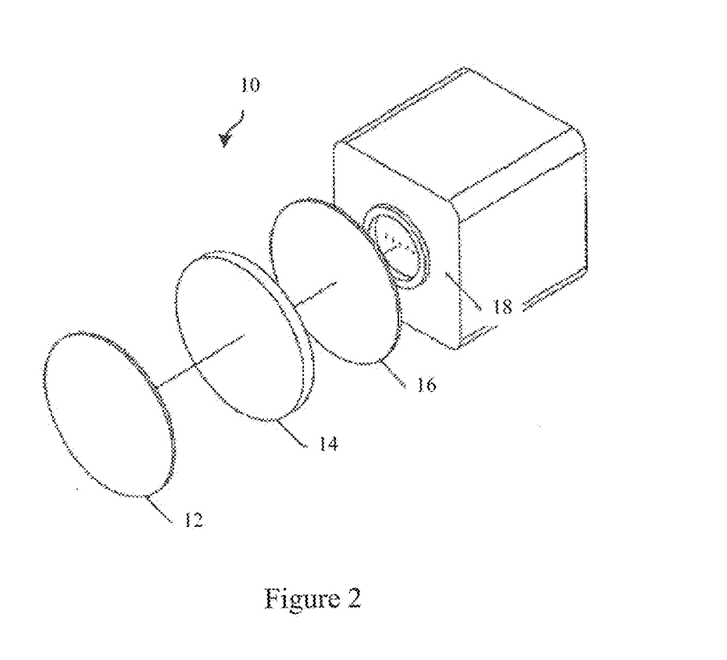
FIG. 2 illustrates an isometric view of the exemplary UV light beam profiler in FIG. 1.

FIG. 1 shows a side profile of an exemplary UV light beam profiler 10. FIG. 2 shows an isometric view of the exemplary UV light beam profiler 10. UV light beam profiler 10 may include a UV-to-visible light converter 12, objective lens 14, filter 16, and an image sensor (or camera) 18. The components may be housed together in a UV light beam profiler housing (not shown). The objective lens 14 and the filter 16 may be positioned between the converter 12 and the camera 18. In some embodiments the filter 16 is positioned between the objective lens 14 and the camera 18.

The UV light beam profiler 10 may work as follows. When the UV light under assessment hits the converter 12, it induces fluorescent visible light with the profile that replicates the original profile of the UV light beam. The profile of fluorescent light may be imaged by the objective lens 14 onto the camera 18. Filter 16 may be used to transmit the light with the wavelength of fluorescent light and block the light with other wavelengths. Camera 18 may be used to convert the image of the fluorescent light profile into an electrical signal that is recorded for further analysis.

The principles of fluorescence imaging are that a UV beam impinges onto fluorescing crystal. The crystal fluoresces in visible wavelengths, proportional to the UV energy in the beam. Then the visible fluorescence may be imaged with a CCD camera and a normal imaging lens. Both the crystal and the glass lens block UV scattered light so that only visible light may be imaged. There are many crystalline materials that fluoresce in the visible in response to UV stimulation. A typical non-crystalline material is Cerium doped glass, which may be inexpensive to use.

In some embodiments, the beam profiler 10 may be a fixed-focus camera based device—the focus may be set as part of the assembly process. The focusing may be a manual operation in which an operator sets and secures the focus of each individual unit. Typically, setting the focus requires high-precision positioning of the beam profiler's converter 12 and objective lens 14 relative to the image sensor 18. Conventional beam profilers may include high-precision structural features that facilitate setting the proper focus. In some embodiments, the high-precision features may be a converter 12 and objective 14 assembly that attaches to the camera housing with screw threads. The threaded attachment may provide a mechanism for positioning the focal point on the image sensor, and may maintain planarity between the converter 12, objective lens 14, and image sensor 18. During the assembly of a beam profiler 10, an operator may thread the converter/objective assembly onto the camera housing until a desired focus is achieved. Thereafter, the operator may fix the threaded converter/objective assembly positioning using adhesives, for example. Thus, screw threads for positioning a converter 12/objective 14 assembly on a camera housing may provide a mechanism for achieving a high accuracy/high precision positioning of the converter/objective without the use of high precision assembly instruments.

Figure 3:
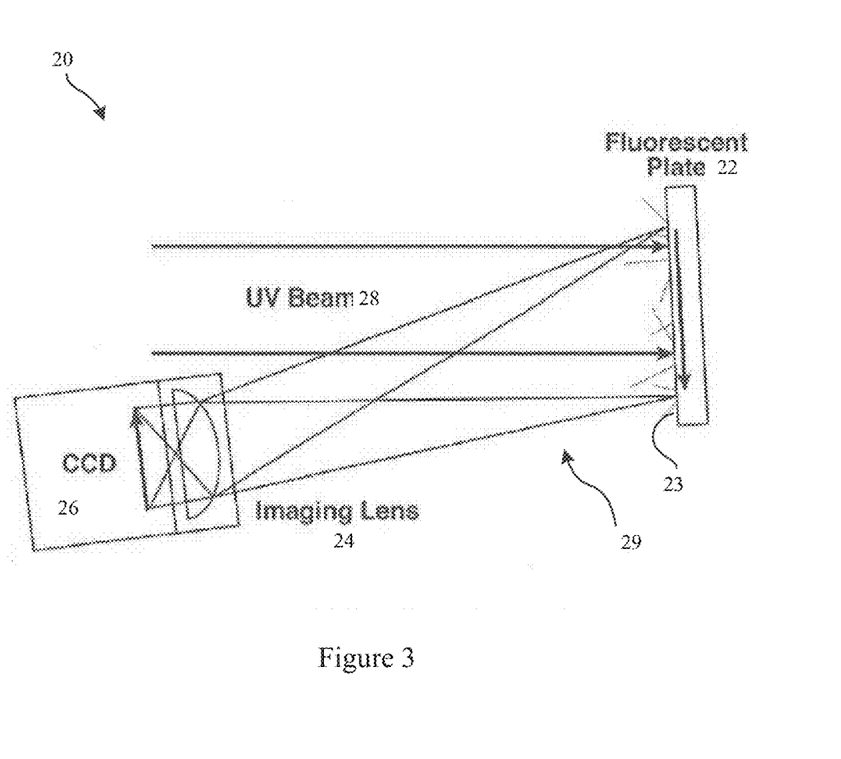
FIG. 3 illustrates another exemplary UV light beam profiler.

FIG. 3 illustrates another exemplary UV light beam profiler 20. UV light beam profiler 20 includes a fluorescent plate 22, an imaging lens 24, and an image sensor 26 (CCD). The setup of FIG. 3 provides a slightly off-axis reflection measurement where the visible light is imaged from the same side as the incident beam. As illustrated in FIG. 3, this setup may position the imaging lens 24 and the image sensor 26 assembly to be on the same side as the input beam 28. In this setup, UV input beam 28 impinges on the fluorescing plate 22. The fluorescing/visible light 29 is then imaged by the lens 24 and CCD 26 assembly from a front surface 23 of the fluorescing plate 22. In some embodiments, a filter may be used to block UV light from the imaging sensor 26.

Figure 4:
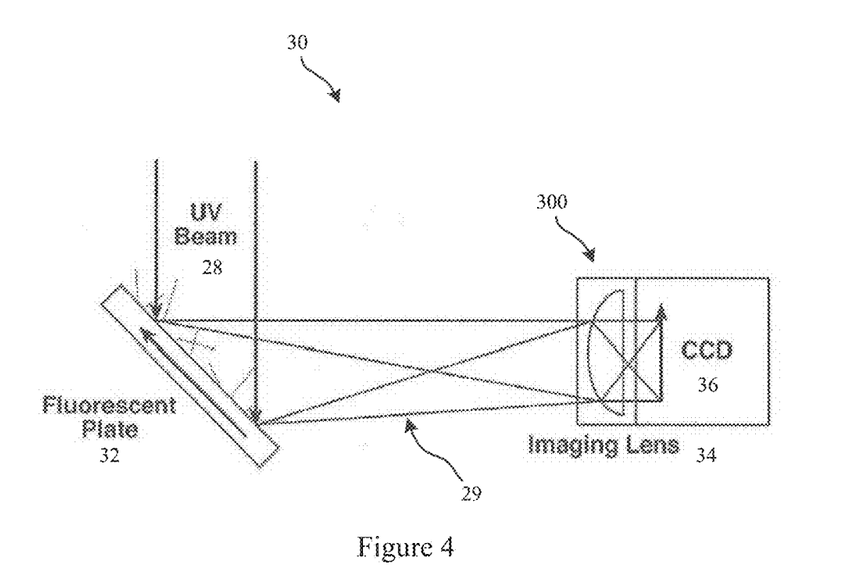
FIG. 4 illustrates yet another exemplary UV light beam profiler.

FIG. 4 illustrates another exemplary UV light beam profiler 30. In the setup of FIG. 4, the fluorescing plate 32 may be at 45° between the incident beam 28 and the imaging lens 34 and CCD sensor 36 assembly. This setup allows the lens 34 and the CCD 36 assembly to image the fluorescing light 29 at 90° relative to the incident beam 28.

Figure 5:
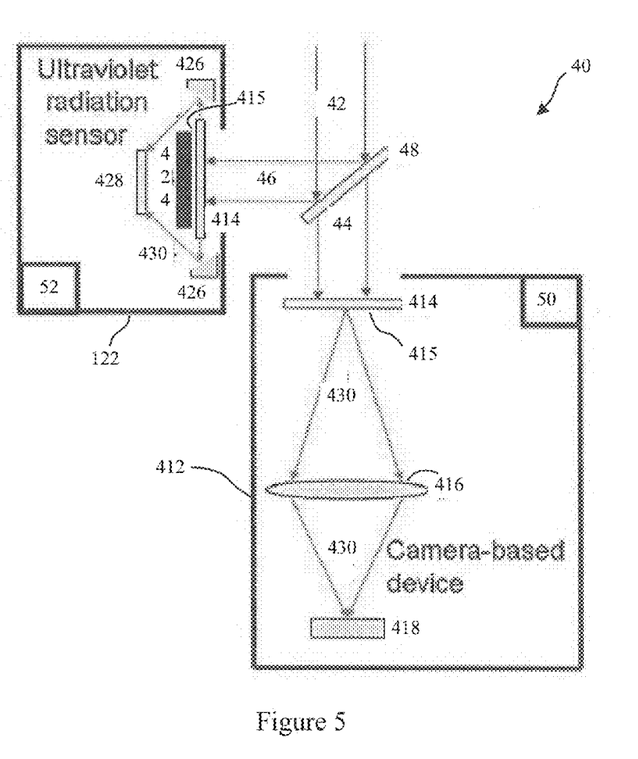
FIG. 5 illustrates an exemplary fluence profiler that may incorporate embodiments of a camera-based UV light beam profiler.

FIG. 5 illustrates an exemplary fluence profiler 40 that may incorporate embodiments of a camera-based UV light beam profiler. Exemplary fluence profiler 40 works as follows. A fraction of a UV beam 42 may be split into two parts 44, 46 by beam splitter 48. The first part 44 of the beam 42 may be analyzed by a camera-based device 50 (e.g., UV light beam profiler 10, 20, 30 or the like) and the second part 46 of the beam 42 may be analyzed by an ultraviolet radiation sensor 52 by measuring the total energy of UV radiation (IB).

With the profile and energy measurements from the camera-based device 50 and the ultraviolet radiation sensor 52, the fluence profile may be calculated by associating the portion of the total energy to pixels of the beam profile depending on the pixel weight. Embodiments of the fluence profiler 40 may provide real-time detection of beam shape, beam size, and/or beam position. The real-time detection may be advantageous, for example, during refractive surgery as it allows for monitoring of a treatment in real-time and if needed, revision of the treatment in real-time when deviations from a desired treatment are calculated. Further, many embodiments of the fluence profiler 40 may have little or no moving parts. And, preferably, the fluence profiler 40 may be resistant to ambient light errors when making beam size, shape, and/or position measurements, etc.

Camera-based device 50 may comprise a housing 412 for housing a UV-to-visible converter 414, an objective lens 416, and an image sensor 418. The first part 44 of the beam 42 falls on the UV-to-visible converter 414 and excites fluorescent light 430 in the visible range. Florescent light 430 propagates in all directions including directions toward the back surface 415 of the converter plate 414. The light emitted from the back surface 415 of the converter 414 is imaged by the objective lens 416 onto image sensor 418. The image sensors 418 is configured to detect the profile (shape) of florescent light that is proportional to the beam profile of the excitation UV radiation.

While illustrated and described with an in-line configuration and without a filter, It should be understood that UV light beam profiler 10, 20, 30 or the like may be used in many embodiments.

Ultraviolet radiation sensor 52 may comprise a housing 422 (e.g. 122 on FIG. 5) for housing a UV-to-visible converter 414, a light blocker 424, a conical mirror 426, and a detector 428. The second part 46 of the beam 42 falls on the UV-to-visible converter plate 414 and excites fluorescent light 430 in the visible range. Fluorescent light 430 propagates in all directions including directions toward the edge of the converter plate 414. Light blocker 424 may be positioned adjacent to a back surface 415 of converter plate 414 and may be configured to block ambient light from reaching detector 428. The light 430 emitted from the edge of the converter plate 414 is redirected with a conical mirror 426 toward detector 428, thereby bypassing light blocker 424. The detector 428 may be configured to detect the energy of fluorescent light 430 that is proportional to the total energy of the excitation UV radiation.

Figure 6:
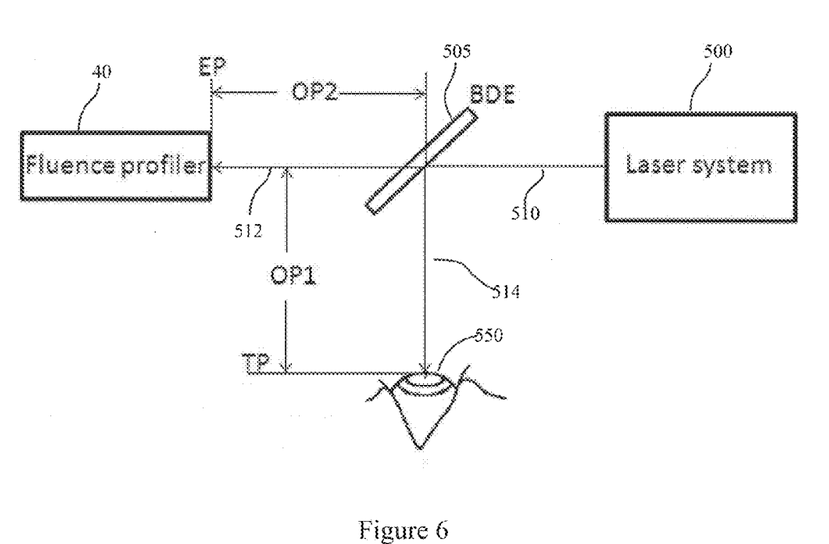
FIG. 6 illustrates an exemplary laser system that may benefit from direct fluence measurement by a fluence profiler according to some embodiments.

FIG. 6 illustrates an exemplary laser system that may benefit from direct fluence measurement by a fluence profiler 40 according to some embodiments. As illustrated in FIG. 6, a laser beam 510 from a laser system 500 may be sent through a beam dividing element (BDE) 505 such that a fraction 512 of the beam 510 can be sent to the fluence profiler 40 along optical path 2 (OP2). The bulk 514 of the original laser beam 510 may go through optical path 1 (OP1) to be delivered onto the patient's cornea 550.

While laser system 500 is illustrated as an ophthalmic surgery laser system it should be understood that many methods and devices disclosed herein may be applicable with other laser systems where it is desirable to measure beam energy, fluence, and profile combined or separately.

Figure 7A:
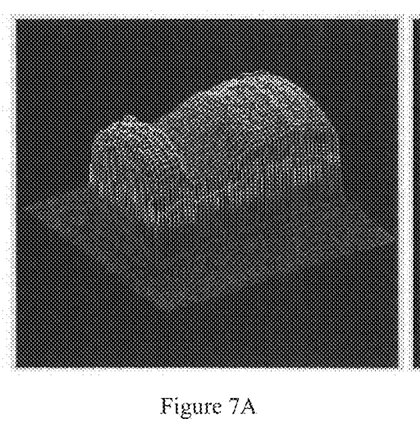
FIG. 7A-7B show an example of UV fluorescent imaging of a laser at 248 nm using an exemplary UV light beam profiler.
Figure 7B:
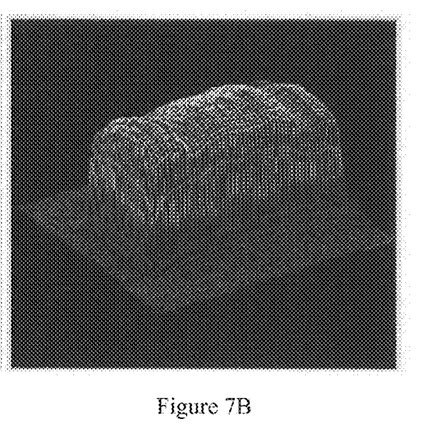

An example of UV fluorescent imaging of a laser at 248 nm is provided in FIGS. 7A-7B. A rectangular aperture was used to pick off a portion of the beam. FIG. 7A is an initial measurement and FIG. 7B is a subsequent measurement after adjustments were made to the laser and optics to provide a more uniform intensity.

As mentioned above, embodiments of the fluence profiler 40 may provide real-time detection of beam energy, beam shape, beam size, and/or beam position and such real-time detection may have many advantageous. For example, during refractive surgery, it may allow for monitoring of a treatment in real-time and if needed, revision of the treatment in real-time when deviations from a desired treatment are calculated. However, for beam profilers (e.g., profiler 10, 20, 30, 50, or the like) to work properly (and consequently a fluence profiler 40 that comprises the UV beam profiler), the converter, objective, and camera should be aligned or focused in such a way that the converter is located at the object plane OP and the camera is located at the image plane IP of the objective lens (see FIG. 1). If converter or camera are out of object or image plane, respectively, the data acquired by the beam profiler may be misinterpreted.

Accordingly, there is a need for a tool that can be used for beam profiler focusing and focus verification. Additionally, the beam profiler should be calibrated frequently (e.g., after assembly, repair, alignment, realignment, for verification purposes, etc.). This tool may be applicable to any beam profiler that uses a converter plate to convert invisible radiation into visible radiation for further detection and analysis.

Figure 8:
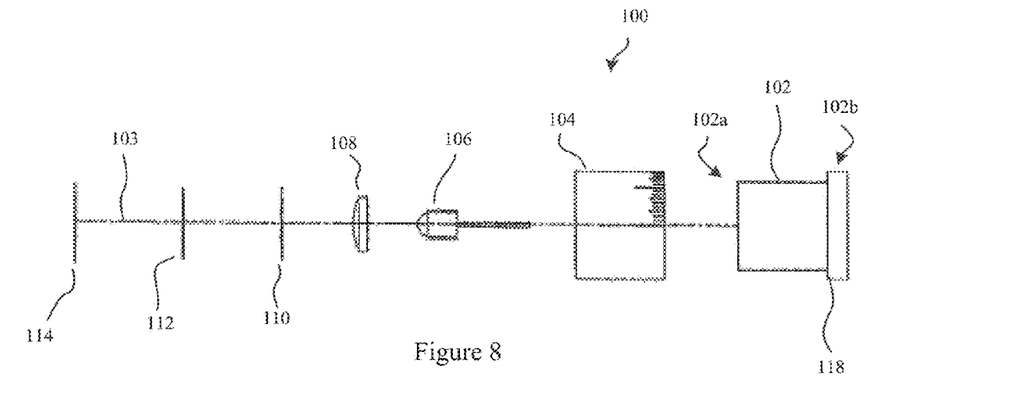
FIG. 8 illustrates an exploded side view of an exemplary test object that may be used for focusing and/or calibration of a UV light beam profiler.
Figure 9:
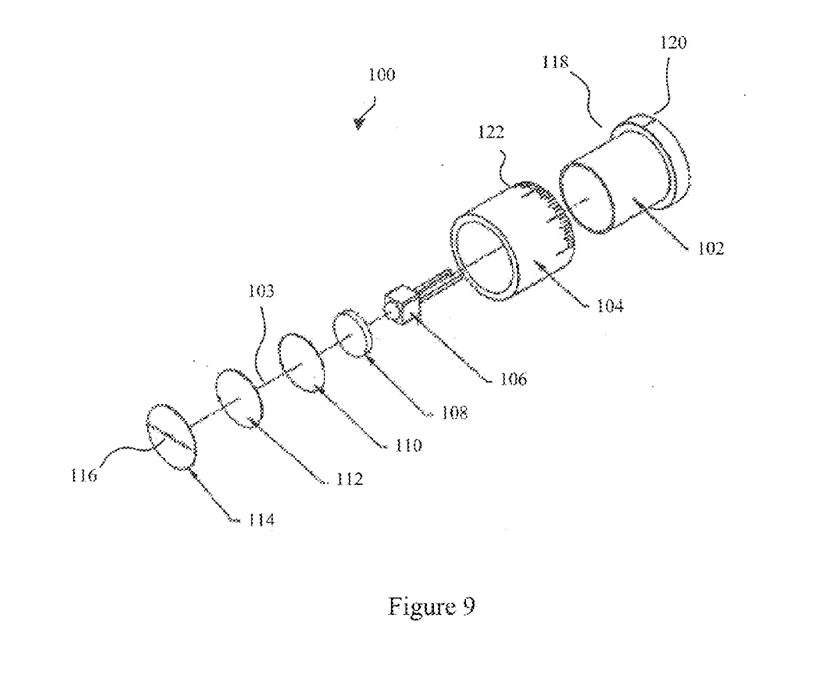
FIG. 9 illustrates an exploded isometric view of the exemplary test object illustrated in FIG. 8.
Figure 10:
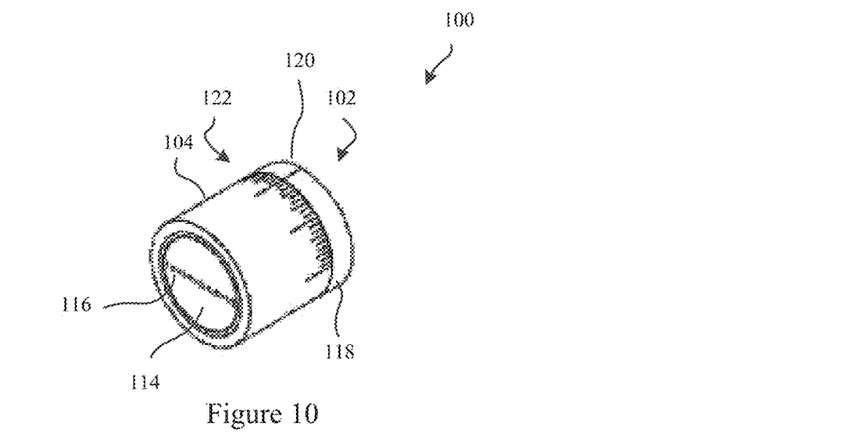
FIG. 10 illustrates exemplary test object of FIG. 8 as assembled.
Figure 11:
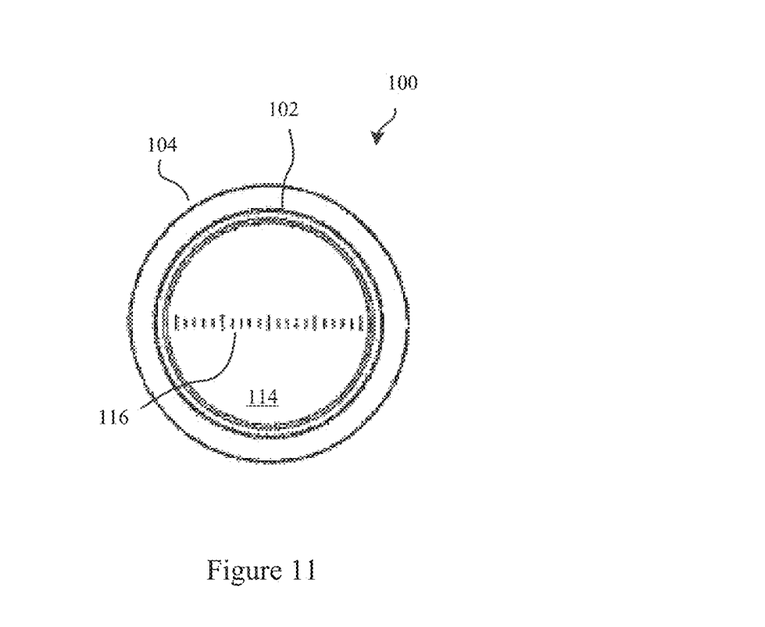
FIG. 11 illustrates a front view of the exemplary test object of FIG. 8 as assembled.

FIG. 8 illustrates an exploded side view of an exemplary test object 100 that may be used for focusing and/or calibration of a UV light beam profiler. FIG. 9 illustrates an exploded isometric view of the exemplary test object 100. FIG. 10 illustrates exemplary test object 100 as assembled. FIG. 11 illustrates a front view of exemplary test object 100. Test object 100 includes an internal housing 102 housed within external housing 104. Internal housing 102 may be rotatable relative to external housing 104 about internal housing 102 axis 103. Internal housing 102 may house a light source 106, a collimator 108, a bandpass filter 110, and a diffuser 112. A plate 114 may be positioned at an end 102a of internal housing 102 and mounted thereto. The plate 114 may include a plurality of markings 116.

The external housing 104 includes an opening for receiving the internal housing 102. In some embodiments, the opening of external housing 104 may be a generally cylindrical shape for receiving a cylindrically shaped internal housing 102. While illustrated as generally having a cylindrical body, it should be understood that other configurations are possible. An external body 104 with a cylindrical configuration may however provide for a more compact design.

The internal housing 102 may comprise a generally cylindrical body that corresponds to the opening of external housing 104 and may be rotatable about internal housing axis 103 within external housing 104. The cylindrical body may include an end 102b opposite end 102a. The end 102b may have a raised surface 118 extending laterally or transverse from axis 103. The raise surface 118 may extend a distance approximately equal to a thickness of a wall of external housing 104 so that when internal housing 102 is housed therein, the raised surface 118 of internal housing 102 may be generally flush with an outer surface of external housing 104. Additionally, the raised surface 118 of internal housing 102 may incorporate indicia 120 that cooperate with indicia 122 on the outer surface of the external housing 104 to provide rotational relationship information between the internal housing 102 and the external housing 104.

In the illustrated embodiment, the external housing 104 includes a plurality of indicia 122 at the end proximate to end 102b of internal housing 102. The plurality of indicia 122 on external housing 104 include major and minor indicia, and the end 102b of internal housing 102 includes a single indicia 120. While the exemplary embodiment 100 includes a plurality of indicia 122 on the external housing 104 and a single indicia 120 on the raised surface 118 of internal housing 102, it should be understood that other configurations are possible. For example, the external housing 104 may have a single indicia that cooperates with a plurality of indicia on internal housing 102.

Light source 106 may be configured to emit light in the broad spectral range (e.g., 350-1000 nm). For example, LEDs, OLEDS, or other non-coherent light sources. The light from the light source 106 may be collimated by collimator 108. The bandpass filter 110 may be a narrow band filter that may transmit the light with the wavelength of the fluorescent light of the beam profiler 10 while blocking the light with other wavelengths. As an example, a Bandpass Colored Glass Filter FGV9 from Thorlabs™ may be used if converter generates the fluorescent light in the range 485-565 nm. The diffuser 112 may evenly disperse the light across plane 114 and the plurality of markings 116. The plurality of markings 116 may be a repeated bar pattern with known parameters and may be designed for transmission of light (e.g., transparent). As an example, a USAF 1951 resolution test pattern may be used or any other resolution pattern, depending on the accuracy requirements for focusing and calibration. Plate 114 may be opaque such that light exiting the test object 100 is in the desired pattern 116.

In some embodiments, a bandpass filter 110 may not be needed. For example, in some embodiments a light source 106 may be configured to emit light in a narrow bandwidth. As an example, an Ultra Bright Red LED LED630E from Thorlabs™ may be used if converter generates the fluorescent light in the range (639±10) nm. Other coherent light sources may be used in some embodiments. In such an embodiment, test object 100 may not need a bandpass filter 110 to transmit particular wavelengths of light.

The test object 100 may be used for both focusing and calibration of a UV light beam profiler 10. Additionally, the test object 100 may be used in the field where the beam profiler 10 is integrated within a host system and cannot be removed from the system.

Figure 12:
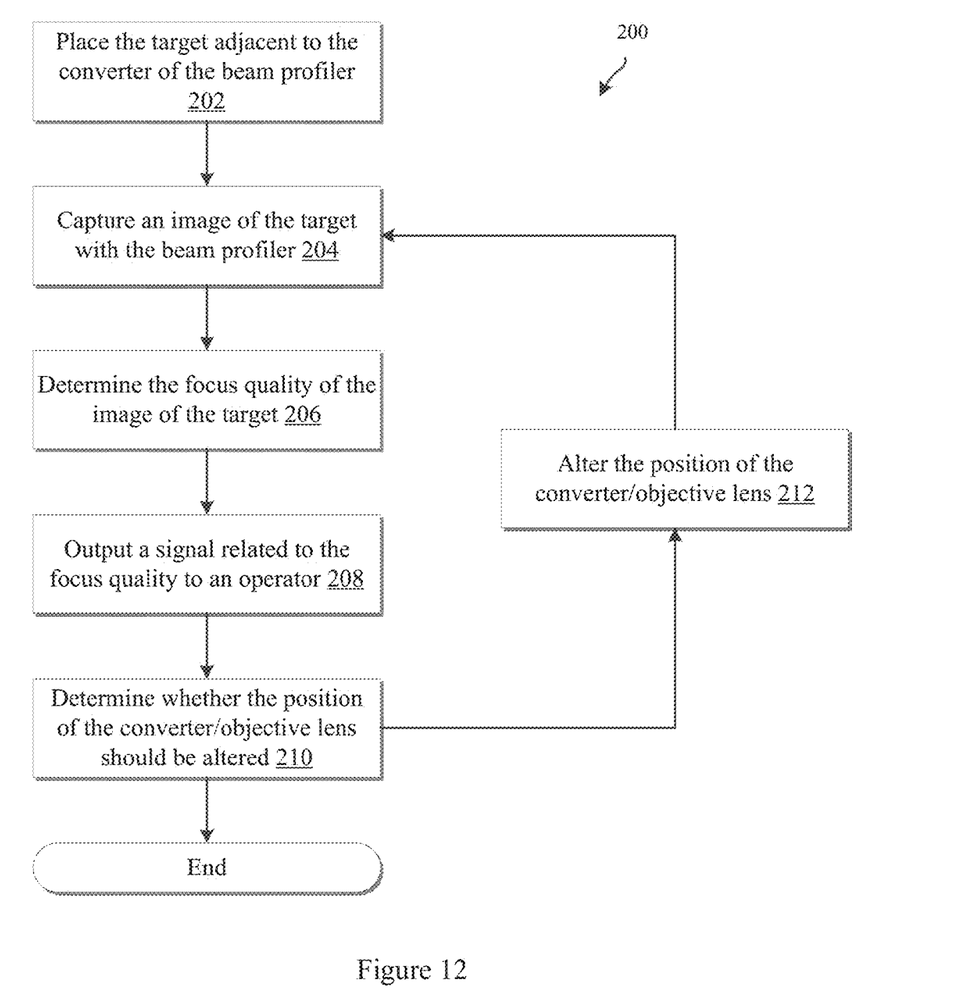
FIG. 12 provides an exemplary work flow for focusing a beam profiler according to some embodiments of the invention.

FIG. 12 provides an exemplary work flow 200 for focusing a beam profiler. At step 202, the test object may be placed in close proximity to the beam profiler in such a way that the plurality of markings (e.g., a repeated bar pattern) of the test object 100 touches the converter of a beam profiler. At step 204, an image of the test object 100 may be captured with the beam profiler. A focus quality of the captured image may be determined 206. A signal related to the focus quality of the image may be output 208 to an operator. At step 210 a determination may be made, based on the focus quality of the image and/or the output signal, as to whether the position of the converter, objective, and/or camera should be adjusted to improve a focus quality of subsequently captured images. At step 212, adjustments to a positioning of the converter, objective, and/or camera are made. Steps 204-212 may be repeated until a desired focus quality is achieved or to verify a focus of the beam profiler.

Figure 13:
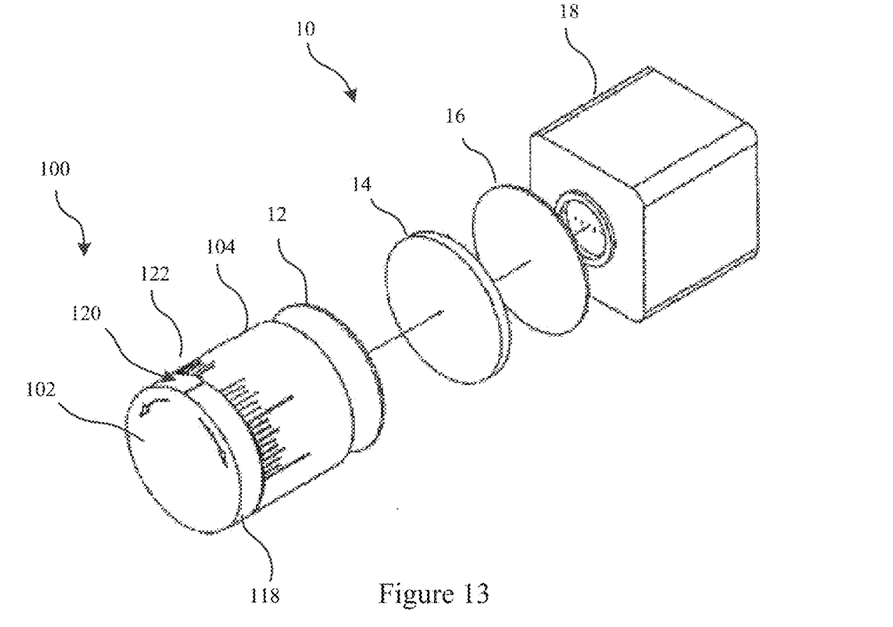
FIG. 13 illustrates an exploded view of a coupling of an exemplary test object with a beam profiler.
Figure 14:
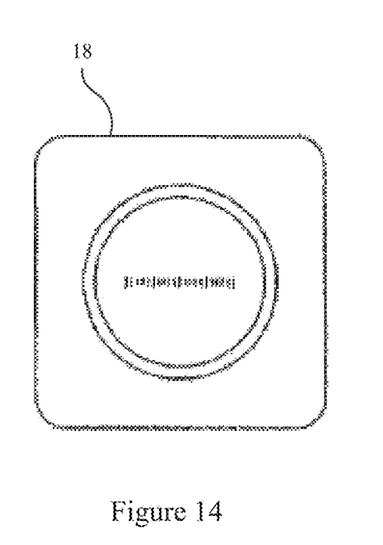
FIG. 14 illustrates a front view of the image sensor of the beam profiler with an image of the plurality of markers of the test object on it.

FIG. 13 illustrates an exploded view of an assembly of an exemplary test object 100 with beam profiler 10. FIG. 14 illustrates a front view of the image sensor 18 of the beam profiler 10 with an image of the plurality of markers of the test object 100 on it. It should be understood that test object 100 may be used for focusing and/or calibrating other beam profilers. The illustrated us with beam profiler 10 is exemplary and non-limiting.

Focus quality may be assessed in many ways. One of them is based on measuring the contrast within a sensor field. The intensity difference between adjacent pixels of the sensor naturally increases with correct image focus. The optical system can thereby be adjusted until the maximum contrast is detected.

In some embodiments, during beam profiler assembly, the converter and objective may be rigidly fixed together so that the converter is positioned at the object plane of the objective. The converter and objective assembly may then be moved relative to the image sensor to adjust the focus of the beam profiler. Optionally, the converter, objective, and/or camera sensor may be individually moved to achieve the desired beam profiler focus. After a desired focus is achieved, a position of the converter, objective, and/or camera may be rigidly fixed.

In many embodiments, the image sensors of beam profilers may express the image coordinates in pixels. While the focusing provides a desired image quality of the beam profile focused onto the image sensor, a calibration procedure specifies the relationship and establishes the conversion factors between pixels and the physical object units, for example, millimeters. The calibration provides a mapping from object space (where fluorescent beam profile is generated) to image space (where fluorescent beam profile is recorded). Knowing the value of these conversion factors is important for accurate beam profile parameter determination. Accurate focusing and calibration of the beam profilers may significantly impact quantitative measurements (e.g., size, shape, uniformity, or the like) extracted from the images. The geometric calibration of a beam profiler may be performed by the methods described below.

Figure 15:
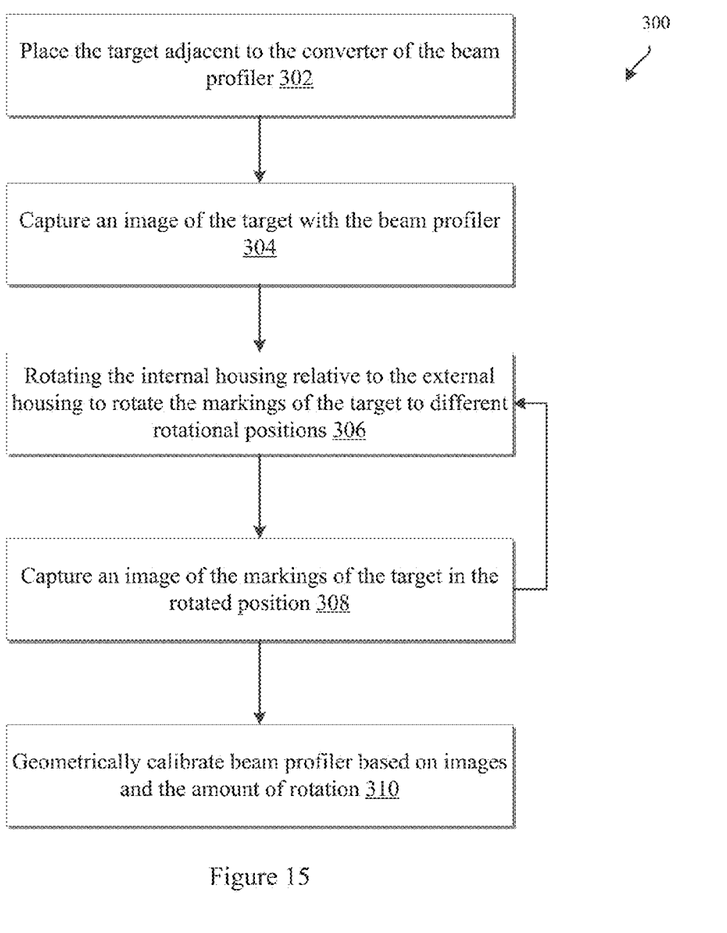
FIG. 15 provides an exemplary work flow for geometrical calibration of a beam profiler.

FIG. 15 provides an exemplary work flow 300 for geometrical calibration of a beam profiler. At step 302, the test object 100 may be placed in close proximity to the beam profiler in such a way that the plurality of markings (e.g., a repeated bar pattern) of the test object 100 touches the converter of a beam profiler. In some embodiments, if the calibration is being performed after a focusing of the beam profiler, the test object 100 may be left in place.

An image of the plurality of markers of the test object may then be captured 304. The plurality of markers of the test object may be rotated to another position by rotating the internal housing relative to the external housing of the test object 306. An image of the plurality of markers of the test object at the rotated position may then be captured 308. Steps 306-308 may be repeated to capture images of the target with the beam profiler for several distinct positions of the target. Thereafter, the calibration for the beam profiler may then be calculated 310 based on the plurality of images of the target.

Figure 16A:
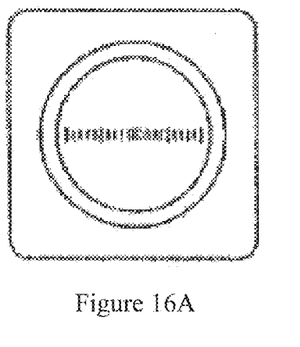
FIGS. 16A-16C illustrate a front view of a beam profiler image sensor with the target image at different rotational positions.
Figure 16B:
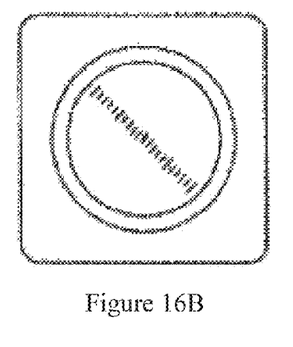
Figure 16C:
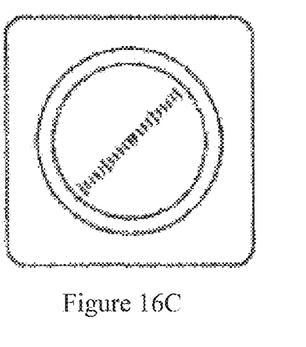

FIGS. 16A-16C illustrate a front view of a beam profiler image sensor with the target image at different rotational positions. FIG. 16A is an image for the horizontal orientation of the image. FIG. 16B and FIG. 16C are images for the angle orientation of the target.

Calibration may be determined by a scale factor measured in pixel per mm -[pix/mm]. A scale factor relates the physical dimensions and locations of the laser spot at a converter plate to the corresponding dimensions and locations on a CCD image. In a general case, the shape of the pixel is rectangular that requires measuring two scale factors along directions of the pixel's sides which in turn, requires detecting target image at different rotational positions. In the case of a square pixel shape, there may be only one scale factor that may be measured by detecting a single target image.

One or more computing devices may be adapted to provide desired functionality by accessing software instructions rendered in a computer-readable form. When software is used, any suitable programming, scripting, or other type of language or combinations of languages may be used to implement the teachings contained herein. However, software need not be used exclusively, or at all. For example, some embodiments of the methods and systems set forth herein may also be implemented by hard-wired logic or other circuitry, including but not limited to application-specific circuits. Combinations of computer-executed software and hard-wired logic or other circuitry may be suitable as well.

Embodiments of the methods disclosed herein may be executed by one or more suitable computing devices. Such system(s) may comprise one or more computing devices adapted to perform one or more embodiments of the methods disclosed herein. As noted above, such devices may access one or more computer-readable media that embody computer-readable instructions which, when executed by at least one computer, cause the at least one computer to implement one or more embodiments of the methods of the present subject matter. Additionally or alternatively, the computing device(s) may comprise circuitry that renders the device(s) operative to implement one or more of the methods of the present subject matter.

Any suitable computer-readable medium or media may be used to implement or practice the presently-disclosed subject matter, including but not limited to, diskettes, drives, and other magnetic-based storage media, optical storage media, including disks (e.g., CD-ROMS, DVD-ROMS, variants thereof, etc.), flash, RAM, ROM, and other memory devices, and the like.

Figure 17:
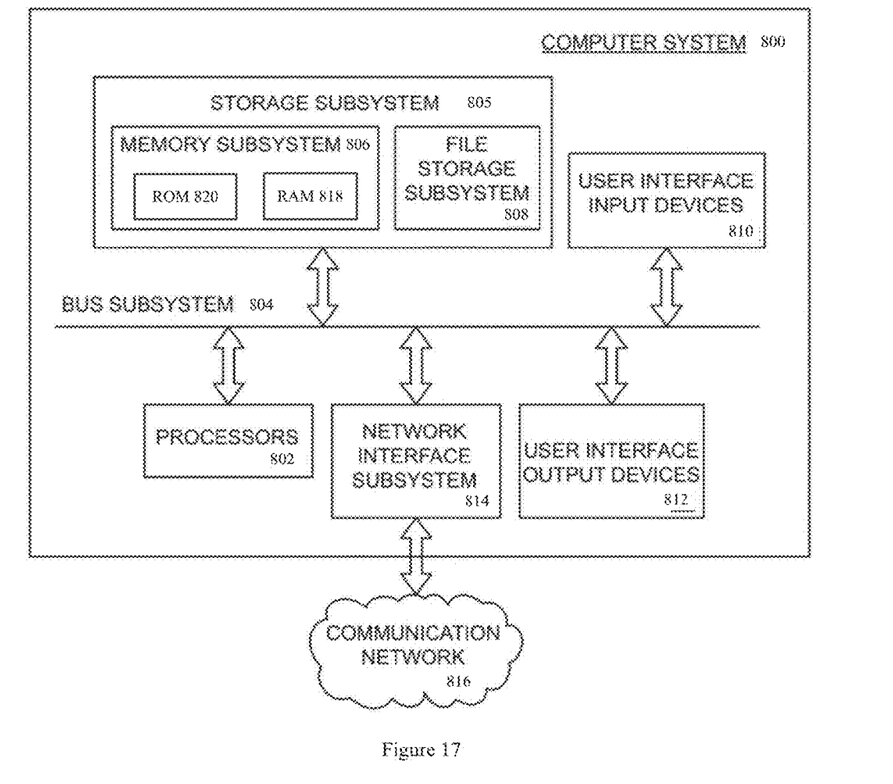
FIG. 17 is a simplified block diagram of an exemplary computer system that may be utilized in embodiments described herein.

To this end, FIG. 17 is a simplified block diagram of an exemplary computer system 800 that may be utilized in embodiments described herein. The computer system 800 typically includes at least one processor 802 which communicates with a number of peripheral devices via a bus subsystem 804. These peripheral devices may include a storage subsystem 805, comprising a memory subsystem 806 and a file storage subsystem 808, user interface input devices 810, user interface output devices 812, and a network interface subsystem 814. Network interface subsystem 814 provides an interface to a communication network 816 for communication with other imaging devices, databases, or the like.

The processor 802 performs the operations of the computer system 800 using execution instructions stored in the memory subsystem 806 in conjunction with any data input from an operator. Such data can, for example, be input through user interface input devices 810, such as the graphical user interface. Thus, processor 802 can include an execution area into which execution instructions are loaded from memory. These execution instructions will then cause processor 802 to send commands to the computer system 800. Although described as a "processor" in this disclosure, the functions of the processor may be performed by multiple processors in one computer or distributed over several computers.

User interface input devices 810 may include a keyboard, pointing devices such as a mouse, trackball, touch pad, or graphics tablet, a scanner, foot pedals, a joystick, a touch-screen incorporated into the display, audio input devices such as voice recognition systems, microphones, and other types of input devices. In general, use of the term "input device" is intended to include a variety of conventional and proprietary devices and ways to input information into the computer system. Such input devices will often be used to download a computer executable code from a computer network or a tangible storage media embodying steps or programming instructions for any of the methods of the present invention.

User interface output devices 812 may include a display subsystem, a printer, a fax machine, or non-visual displays such as audio output devices. The display subsystem may be a cathode ray tube (CRT), a flat-panel device such as a liquid crystal display (LCD), a projection device, or the like. The display subsystem may also provide non-visual display such as via audio output devices. In general, use of the term "output device" is intended to include a variety of conventional and proprietary devices and ways to output information from the computer system to a user.

Storage subsystem 805 stores the basic programming and data constructs that provide the functionality of the various embodiments. For example, database and modules implementing the functionality of embodiments described herein may be stored in storage subsystem 805. These software modules are generally executed by processor 802. In a distributed environment, the software modules may be stored in a memory of a plurality of computer systems and executed by processors of the plurality of computer systems. Storage subsystem 805 typically comprises memory subsystem 806 and file storage subsystem 808.

Memory subsystem 806 typically includes a number of memories including a main random access memory (RAM) 818 for storage of instructions and data during program execution and a read only memory (ROM) 820 in which fixed instructions are stored. File storage subsystem 68 provides persistent (non-volatile) storage for program and data files, and may include a hard disk drive, a floppy disk drive along with associated removable media, a Compact Digital Read Only Memory (CD-ROM) drive, an optical drive, DVD, CD-R, CD-RW, or removable media cartridges or disks. One or more of the drives may be located at remote locations on other connected computers at other sites coupled to the computer system. The databases and modules implementing the functionality of the present invention may also be stored by file storage subsystem 808.

Bus subsystem 804 provides a mechanism for letting the various components and subsystems of the computer system communicate with each other as intended. The various subsystems and components of the computer system need not be at the same physical location but may be distributed at various locations within a distributed network. Although bus subsystem 804 is shown schematically as a single bus, alternate embodiments of the bus subsystem may utilize multiple busses.

The computer system 800 itself can be of varying types including a personal computer, a portable computer, a workstation, a computer terminal, a network computer, a module in a display unit, a mainframe, or any other data processing system. Due to the ever-changing nature of computers and networks, the description of the computer system 800 depicted in FIG. 30 is intended only as a specific example for purposes of illustrating one embodiment of the present invention. Many other configurations of the computer system are possible having more or fewer components than the computer system 800 depicted in FIG. 30.

Different arrangements of the components depicted in the drawings or described above, as well as components and steps not shown or described are possible. Similarly, some features and sub-combinations are useful and may be employed without reference to other features and sub-combinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications may be made without departing from the scope of the claims below.

What is claimed is:

1. A beam profiler system comprising:
   a beam profiler comprising:
      a UV-to-visible converter plate configured to emit fluorescing light when excited by UV radiation;
      an image sensor; and
      a lens for imaging a profile of the fluorescing light from the UV-to-visible converter onto the image sensor;
      wherein the UV-to-visible converter plate and the lens are moveable relative to the image sensor; and
   a focusing and geometric calibration test object for use with the beam profiler comprising:
      an external housing;
      an internal housing rotatably mounted within the external housing and rotatable relative to the external housing about an internal housing axis;
      a light source housed within the internal housing;
      a plate coupled with the internal housing and transverse to the internal housing axis; and
      a plurality of markings on the plate.

2. The beam profiler system of claim 1, wherein the beam profiler further comprises a filter positioned between the UV-to-visible converter plate and the image sensor, the filter configured to selectively transmit light to the image sensor.

3. The beam profiler system of claim 1, wherein the focusing and geometric calibration test object further comprises a light diffuser, and a collimating lens housed in the internal housing and positioned between the light source and the plate, the diffuser configured to evenly disperse light from the light source across the markings on the plate, and the collimating lens configured to collimate the light emitted by the light source.

4. The beam profiler system of claim 3, wherein the light source is configured to output light in a broad spectral range and wherein the test object further comprises a bandpass filter configured to selectively transmit light from the light source in a particular range of wavelengths.

5. The beam profiler system of claim 4, wherein the diffuser is positioned between the plate and the bandpass filter, and wherein the bandpass filter is positioned between the diffuser and the collimator, and wherein the collimator is positioned between the light source and the bandpass filter.

6. The beam profiler system of claim 3, wherein the light source is configured to output light in a narrow bandwidth and wherein the test object does not include a bandpass filter.

7. The beam profiler system of claim 3, wherein the lens and the image sensor of the beam profiler are along a single axis with the converter plate of the beam profiler.

8. The beam profiler system of claim 3, wherein the lens and the image sensor of the beam profiler measure light fluoresced from a surface of the converter plate.

9. The beam profiler system of claim 3, wherein the lens and the converter plate are fixed together to form a lens-converter plate assembly, and wherein the lens-converter plate assembly moves relative to the image sensor of the beam profiler for focusing the beam profiler.

10. A method of focusing and/or calibrating a beam profiler using a test object comprising an external housing, an internal housing rotatably mounted within the external housing and rotatable relative to the external housing about an internal housing axis, a light source housed within the internal housing, a plate coupled with the internal housing and transverse to the internal housing axis, and a plurality of markings on the plate, the method comprising:
   (a) positioning the plate of the test object adjacent to a UV-to-visible converter plate of the beam profiler;
   (b) imaging the plurality of markings on the plate of the test object with the beam profiler;
   (c) determining a focus quality of the image of the plurality of markings; and
   (d) adjusting a distance between the UV-to-visible converter plate of the beam profiler and an objective lens of the beam profiler.

11. The method of claim 10, further comprising repeating steps (b)-(d) until a desired focus of the beam profiler is obtained.

12. The method of claim 10, further comprising energizing the light source of the test object prior to imaging the plurality of markings on the plate of the test object.

13. The method of claim 10, further comprising:
   (e) imaging the plurality of markings on the plate of the test object with the beam profiler with the plurality of markings at a first position;
   (f) rotating the internal housing relative to the external housing by a rotational amount to rotate the plurality of markings on the plate to a rotated position;
   (g) imaging the plurality of markings on the plate at the rotated position with the beam profiler; and
   (h) geometrically calibrating the beam profiler based on the image of the test object at the first position, the image of the test object at the rotated position, and the rotational amount.

14. The method of claim 13, further comprising repeating steps (f)-(g) so as to provide a plurality of images of the test object at various rotated positions and wherein calibration of the beam profiler is based on the image of the test object at the first position, the plurality of images of the test object at various rotated positions, and the rotational amounts.

15. A method of focusing and/or calibrating a beam profiler using a test object comprising an external housing, an internal housing rotatably mounted within the external housing and rotatable relative to the external housing about an internal housing axis, a light source housed within the internal housing, a plate coupled with the internal housing and transverse to the internal housing axis, and a plurality of markings on the plate, the method comprising:
   positioning the plate of the test object adjacent to a UV-to-visible converter plate of the beam profiler;
   imaging the plurality of markings on the plate of the test object at a first orientation with the beam profiler;
   rotating the internal housing relative to the external housing by a rotational amount to rotate the plurality of markings on the plate to a rotated position;
   imaging the plurality of markings on the plate of the test object at the rotated position with the beam profiler; and
   geometrically calibrating the beam profiler based on the image of the plurality of markings at the first orientation, the image of the plurality of markings at the rotated position, and the rotational amount.

16. The method of claim 15, further comprising energizing the light source of the test object prior to imaging the plurality of markings on the plate of the test object.

17. A system for focusing a beam profiler using a test object comprising an external housing, an internal housing rotatably mounted within the external housing and rotatable relative to the external housing about an internal housing axis, a light source housed within the internal housing, an plate coupled with the internal housing and transverse to the internal housing axis, and a plurality of markings on the plate, the system comprising:

a processing device; and a non-transitory computer-readable medium accessible by the processing device;

wherein the processing device is configured to execute logic embodied in the non-transitory computer-readable medium and thereby perform operations comprising:

(a) imaging the plurality of markings on the plate of the test object with the beam profiler at a first position when the plate of the test object is adjacent to a UV-to-visible converter plate of the beam profiler;

(b) determining a focus quality of the image of the plurality of markings;

(c) outputting a signal corresponding the determined focus quality of the image of the plurality of markings to an operator, the signal being indicative of a need to adjust a distance between the UV-to-visible converter plate of the beam profiler and an objective lens of the beam profiler;

(d) receiving input related to a rotational amount in which the internal housing is rotated relative to the external housing to rotate the plurality of markings on the plate to a rotated position;

(e) imaging the plurality of markings on the plate at the rotated position with the beam profiler; and (f) geometrically calibrating the beam profiler based on the image of the test object at the first position, the image of the test object at the rotated position, and the input related to the rotational amount.

* * * * *